(12) United States Patent
Tang et al.

(10) Patent No.: US 8,491,507 B2
(45) Date of Patent: Jul. 23, 2013

(54) LOW PROFILE CHEST COMPRESSOR

(75) Inventors: Wanchun Tang, Palm Desert, CA (US); Carlos Castillo, Palm Springs, CA (US); Max Harry Weil, Rancho Mirage, CA (US); Joe Bisera, Camarillo, CA (US)

(73) Assignee: Institute of Critical Care Medicine, Rancho Mirage, CA (US)

( * ) Notice: Subject to any disclaimer, the term of this patent is extended or adjusted under 35 U.S.C. 154(b) by 1965 days.

(21) Appl. No.: 11/726,432

(22) Filed: Mar. 22, 2007

(65) Prior Publication Data

US 2007/0249973 A1    Oct. 25, 2007

Related U.S. Application Data

(60) Provisional application No. 60/785,406, filed on Mar. 23, 2006.

(51) Int. Cl.
*A61H 31/00* (2006.01)

(52) U.S. Cl.
USPC ................. 601/43; 601/41; 601/107

(58) Field of Classification Search
USPC ............... 601/41, 43, 44, 105, 106, 148, 149, 601/150, 151, 152, 107–111
See application file for complete search history.

(56) References Cited

U.S. PATENT DOCUMENTS

| | | | |
|---|---|---|---|
| 4,570,615 A | | 2/1986 | Barkalow |
| 4,664,098 A | * | 5/1987 | Woudenberg et al. ........ 601/106 |
| 7,060,041 B1 | | 6/2006 | Weil et al. |
| 7,104,967 B2 | | 9/2006 | Rothman et al. |
| 2005/0015026 A1 | * | 1/2005 | Well et al. ..................... 601/44 |

* cited by examiner

*Primary Examiner* — Quang D Thanh
(74) *Attorney, Agent, or Firm* — Leon D. Rosen

(57) ABSTRACT

An automatic chest compressor (10) for repeatedly compressing the chest of a patient, is constructed to have a small thickness (H) and light weight so it can be readily carried by an emergency worker. The chest compressor includes a piston support (34) at the top, a pressing part (40) at the bottom that presses towards the chest of the patient, and piston side walls (36) that repeatedly elongate to depress the pressing part. The piston side wall are flexible material that is repeatedly curled and uncurled as the side walls move the pressing part respectively up and down.

8 Claims, 2 Drawing Sheets

LOW PROFILE CHEST COMPRESSOR

CROSS-REFERENCE

Applicant claims priority from U.S. Provisional Patent Application Ser. No. 60/785,406 filed Mar. 23, 2006.

BACKGROUND OF THE INVENTION

An automatic chest compressor is used to repeatedly compress and release the chest of a patient to aid in breathing while other measures are taken. Such chest compressor is usually applied by an emergency worker who leaves an ambulance while carrying considerable life saving equipment (e.g. oxygen tank and regulator, defibrillator, bandages, medicines and needles, etc.) that may be useful to the patient whom he is initially approaching. In order to encourage emergency workers to carry a chest compressor, the chest compressor must be of moderate volume, especially small thickness, as well as of low weight. In order for a chest compressor to be effective, it must compress the chest sufficiently (e.g. at least one or two inches) and with sufficient force (a plurality of 10's of pounds), to obtain useful compressions of the patient's chest.

Previous chest compressors have included a metal piston that is repeatedly moved down by high pressure fluid such as pressured air applied above the piston. Such devices have an initial height considerably greater than the piston stroke length, and a considerable weight. An automatic chest compressor that could provide forceful long stoke chest compressions, but that had a small weight and volume, especially a small thickness, would be of value.

SUMMARY OF THE INVENTION

In accordance with one embodiment of the invention, an automatic chest compressor is provided that can apply chest compressions of sufficient length and force to be useful to a patient who is not breathing or not breathing sufficiently, which has a small weight and volume, and especially a small thickness. The automatic chest compressor includes a piston with side walls that elongate and compress in length by curling and uncurling.

The piston has a top and has a bottom with a pressing plate that presses towards the patient's chest. A controlled pressured gas source flows gas such as air into the piston to elongate it and allows the gas to exit to allow the side walls of the piston to compress in length as by curling and uncurling. The chest compressor includes a piston guide of highly elastic elastomeric material that surrounds the piston. The piston guide has an upper end mounted on a piston support to which the top of the piston is mounted, and has a lower end connected to a pressing plate at the bottom of the piston. The guide resists large sideway movement of the pressure plate as it moves down, and provides a spring force that rapidly returns the pressing plate to its upward position after each downward depression.

The novel features of the invention are set forth with particularity in the appended claims. The invention will be best understood from the following description when read in conjunction with the accompanying drawings.

DESCRIPTION OF THE PREFERRED EMBODIMENT

Figure 1:
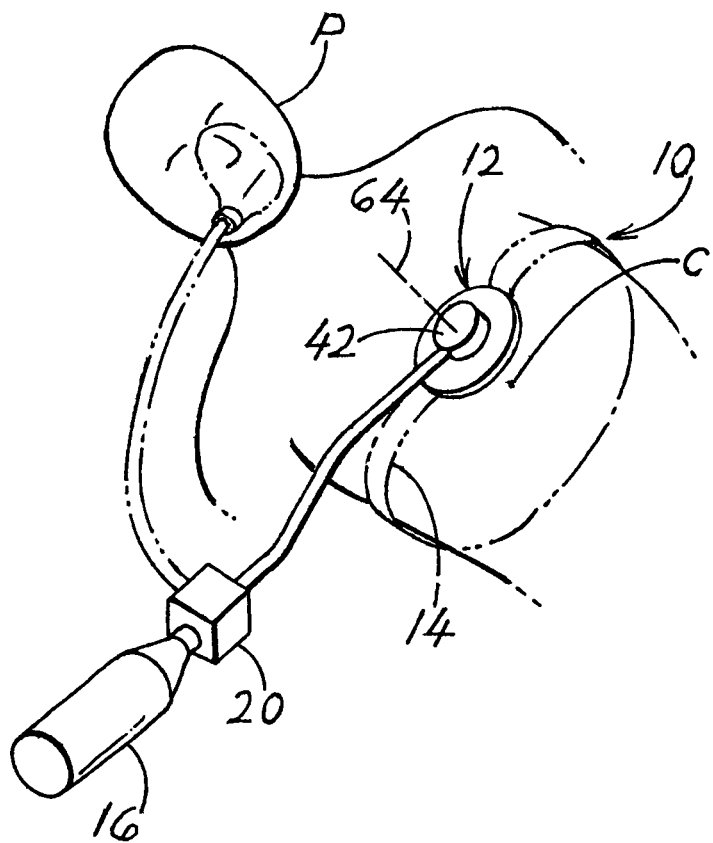
FIG. 1 is an isometric view of a patient with a chest compressor of the present invention strapped on him.
Figure 3:
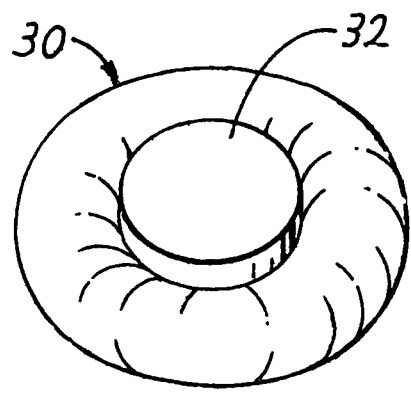
FIG. 3 is an isometric view of just the piston of the chest compressor of FIG. 2.

FIG. 1 shows a chest compressor 10 of the invention, which has been applied to a patient P by placing a compressor apparatus 12 over the patient's chest C and wrapping a strap 14 around the patient. The compressor device is energized with compressed gas (e.g. air) from a bottle 16 that is supplied though a regulator 20 to the apparatus.

Figure 2:
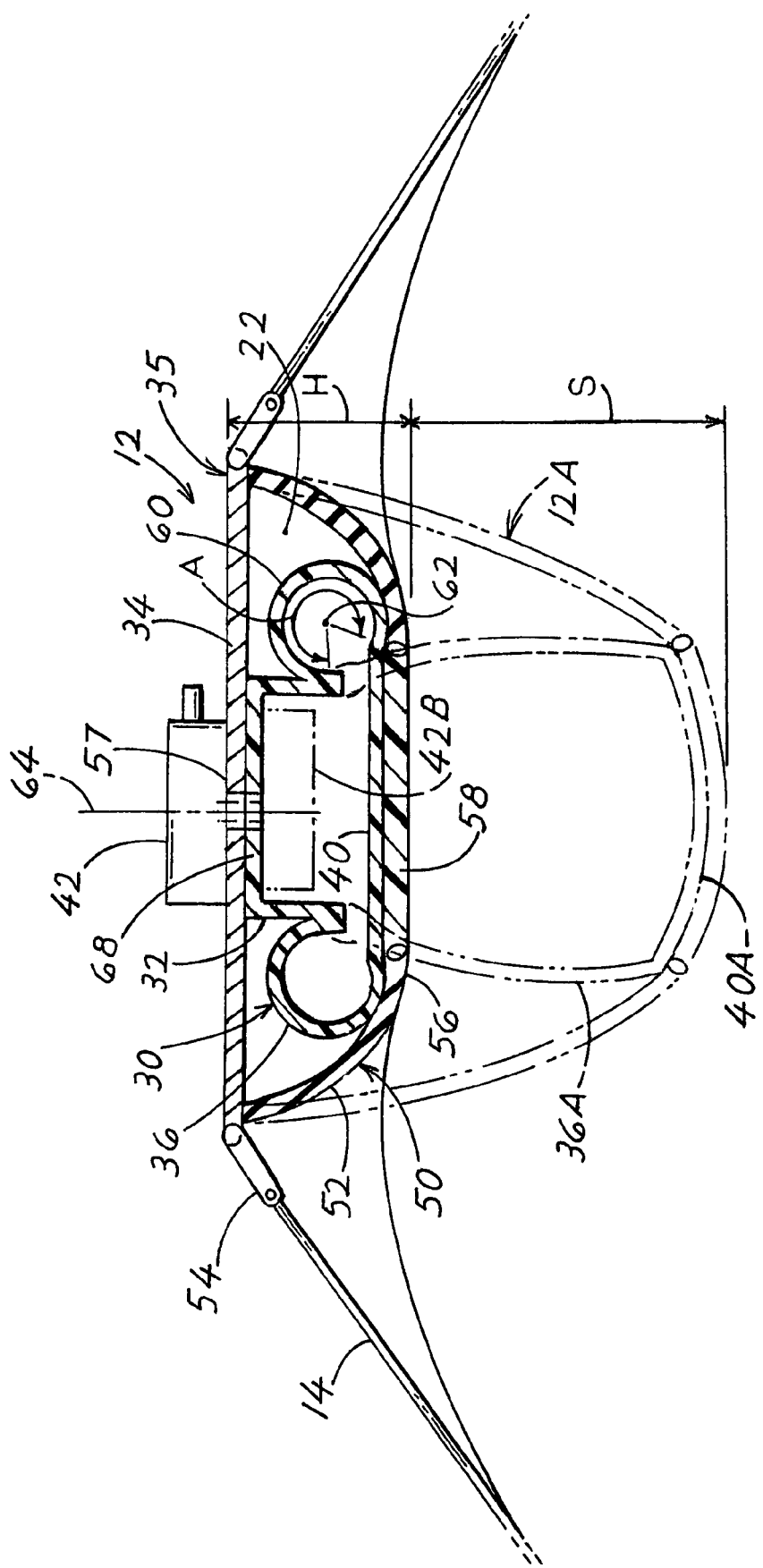
FIG. 2 is a sectional view of the chest compressor and strap of FIG. 1 in its compacted position, with the chest compressor in its extended position shown in phantom lines.

FIG. 2 illustrates the compressor apparatus 12 in solid lines before a compressing stroke and substantially as carried in a stowed configuration by an emergency worker, in a storage region 22. FIG. 2 also shows, in phantom lines, the apparatus 12A when it has been deployed and it applies a large downward stroke to the patient's chest. The apparatus includes a piston element or piston 30 of flexible material, that includes a mount portion 32 that is mounted on a base plate 34 of a piston support 35. The piston element includes a flexing portion 36 that is initially in the stowed position and that holds a pressing part 40. When the compressor apparatus is operating, the pressing part 40 repeatedly presses firmly towards the chest of the patient and then releases the patient's chest to allow it to expand.

The energy for repeatedly moving down the pressing part with considerable force, is obtained from pressured fluid such as air that is applied though a controller 42 to the inside of the piston element 30. The high air pressure in the piston element causes the flexing portion 36 of the piston to elongate downwards from its stowed position towards its fully deployed position 36A at which the flexing portion has moved the pressing part downward to position 40A to compress the chest of the patient.

The apparatus includes a piston guide 50 with a periphery 52 of highly elastic elastomeric material (Young's Modulus of less than 50,000 psi). The piston guide acts as a spring that helps the piston element quickly return to its initial position when fluid pressure is removed after every downward stroke, and stabilizes the piston element position against moving sideways. The guide 50 has a bottom plate 58 that backs up the pressing part 40 of the piston.

The piston element flexible side walls 36 are curled by at least about 180° and preferably by more than 180°, about an axis 62, the curling angle A being 270° in the particular piston illustrated. Such curling is different than multiple folds of a bellows, as shown in U.S. Pat. No. 4,664,098 wherein there are substantially straight sections joined by sharp (small radius of curvature) folds. In the present piston, the curling axis 62 extends in a circle and the side walls are symmetric about the piston axis 64. As pressured air flows into the piston, the side walls 36 uncurl as they move their lower end downward to move down the pressing part 40 and compress the patient's chest. The end of the curled side walls opposite the pressing part 40 is joined by the mount portion 32 to a part 68 that lies against the piston support plate 34. The outside diameter of the curled side walls is at least half the height of the piston in the stowed position.

The piston 30 is preferably of an only moderately elastic elastomeric material, which allows it to elongate somewhat, while being tough enough to minimize leaking of the high pressure gas that produces the downward stroke. The fact that a considerable length of the piston is formed by the side walls 36 that lie in a thin stowed configuration (thickness H) for large elongation, could result in uncontrolled sideward movement of the piston element lower end at its pressing part 40. However, the periphery 52 of the guide 50 has an initial shape without folds, so it holds the pressing part below the center 54 of the base plate while the piston element elongates and retracts. The particular guide illustrated has a center part 58 that lies under the pressing part 40 of the piston element and whose function is to connect opposite sides of the periphery 52 of the guide. The center part is shown holding a flexible pressing plate 58, although the area at 58 could be occupied by the pressing part 40 of the piston. Both the piston 30 and piston guide 50 are preferably formed of a polymer having a density of no more than 2.0. The guide 50 is of material having a high elasticity, that is its Young's Modulus of Elasticity is less than, and preferably less than half that, of the piston side walls.

The fact that the piston flexible side walls elongate when applying a downward stroke to the patient's chest results is a long stroke S for a compressor apparatus of small initial, stowed height H. The stroke length S can be readily made to be greater than the initial height H of the apparatus. The chest compression should be one to two inches, so the stroke length S should be about three to four inches to account for part of the stroke length taken by the strap 14 pressing into the patient. Thus, for a given required stroke length, the compressor apparatus can have a small height so it can be readily carried by an emergency worker. The flexible and elastic polymer material used for the piston element and the piston guide also results in a device of small weight. The controller 42 can be positioned at 42B within the mount portion of the piston element, to further reduce the height of the compressor apparatus when it is carried by an emergency worker.

Although directional words such as "top", "bottom" etc. have been used to describe the invention as illustrated, it should be noted that the chest compressor sometimes can be used in a different orientation.

Thus, the invention provides a chest compressor which has a small thickness and weight and which produces chest compressions of considerable height. The chest compressor includes a piston with side walls that are curled, preferably by more than 180°, about a horizontal stowed piston axis (that may extend in a circle) in the stowed position of the piston, with the side walls uncurling to allow the bottom of the piston to move down to a deployed position to compress a patient's chest. The piston is preferably guided in up and down movement and biased upward, by a guide of elastomeric material that surrounds the piston. Both the piston and the guide can be made primarily of polymer material, which has a density of about one, to minimize the weight of the compressor.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A chest compressor that has a piston support with a top and a storage region below said top, a piston element mounted on said support and having a pressing part that presses against a patient's chest and piston side walls that support said pressing part in up and down movement with respect to the piston support, a pressure gas source that supplies pressured gas to said piston element, wherein the pressing part moves from a minimum distance below said piston support top in a compacted configuration to a distance of at least an inch below said minimum distance in an extended position, wherein:
   said piston side walls are flexible and lie in a curled configuration with part of the piston side walls curled by more than 180° as seen in a sectional view and lying in said storage region when stowed, and are uncurled to increasingly straighten them as the piston side walls approach said extended position.

2. The chest compressor described in claim 1 wherein:
   said piston element is constructed of elastomeric material which stretches as said piston side walls are unrolled.

3. The chest compressor described in claim 1 wherein:
   said pressured gas source includes a controller that lies at least partially within said storage region.

4. A chest compressor comprising:
   a piston support that has a top;
   a piston which has a piston top that is fixed to said piston support top, piston side walls, and a piston bottom which includes a pressing plate for pressing toward a patient's chest, the piston being stowable in a compact stowed configuration and being extendable to a deployed configuration to press on a patient's chest;
   a controlled pressured gas source which includes a source of pressured gas and a controller that control the flow of air into and out of said piston;
   said piston side walls being curled by more than 180° and being constructed to uncurl as the piston moves from said stowed to said deployed configuration.

5. A chest compressor that has a piston support with a top and a storage region below said top, a piston element mounted on said support and having a pressing part that presses against a patient's chest and piston side walls that support said pressing part in up and down movement with respect to the piston support, a pressure gas source that supplies pressured gas to said piston element, and means for evacuating the gas, wherein the pressing part moves from a minimum distance below said piston support top in a compacted configuration to a distance of at least an inch below said minimum distance in an extended position, wherein:
   said piston side walls are flexible and lie in a curled configuration with part of the piston side walls curled at least 180° and lying in said storage region when stowed, and are uncurled to increasingly straighten them as the piston side walls approach said extended position; and including;
   a piston guide which has portions that are spaced about said piston and that each extends between said piston support top and said pressing part of said piston, said piston guide being constructed of elastomeric material that biases said pressing part upward toward its stowed position.

6. The chest compressor described in claim 5 wherein:
   said piston element side walls are of elastomeric material and said piston guide portions are more elastic than said piston element side walls.

7. A chest compressor comprising:
   a piston support that has a top;
   a piston which has a piston top that is fixed to said piston support top, piston side walls, and a piston bottom which includes a pressing plate for pressing toward a patient's chest, the piston being stowable in a compact stowed configuration and being extendable to a deployed configuration to press on a patient's chest;
   a controlled pressured gas source which includes a source of pressured gas and a controller that control the flow of air into and out of said piston;
   said piston side walls being curled and uncurled as the piston moves from said stowed to said deployed configuration;

said piston side walls have lower portions curled in a first direction and have a mount portion extending primarily straight up to said piston support top, as seen in a sectional view.

8. A chest compressor comprising:
a piston support that has a top;
a piston which has a piston top that is fixed to said piston support top, piston side walls, and a piston bottom which includes a pressing plate for pressing toward a patient's chest, the piston being stowable in a compact stowed configuration and being extendable to a deployed configuration to press on a patient's chest;
a controlled pressured gas source which includes a source of pressured gas and a controller that control the flow of air into and out of said piston;
said piston side walls being curled and uncurled as the piston moves from said stowed to said deployed configuration;
said piston having a vertical axis and said piston support top has a top plate with an outer part that extends further from said axis than an upper end of said piston; and including:
a piston guide which has portions that are spaced radially outward of said piston and about said piston and that each extends between said top plate and said pressing plate of said piston, said piston guide portions being constructed of elastomeric material that biases said pressing part upward towards its stowed position.

\* \* \* \* \*